United States Patent
Xie et al.

(10) Patent No.: US 11,692,178 B2
(45) Date of Patent: Jul. 4, 2023

(54) GENETICALLY ENGINEERED BACTERIUM FOR PRODUCING L-HISTIDINE AND USE THEREOF

(71) Applicants: ZHEJIANG ZHENYUAN BIOTECH CO., LTD., Shaoxing (CN); Tianjin University of Science and Technology, Tianjin (CN)

(72) Inventors: Xixian Xie, Tianjin (CN); Weiming Fan, Shaoxing (CN); Heyun Wu, Tianjin (CN); Wei Jiang, Shaoxing (CN); Daoguang Tian, Tianjin (CN); Yanna Chen, Shaoxing (CN); Yue Zhang, Tianjin (CN); Jianqing Tu, Shaoxing (CN)

(73) Assignees: ZHEJIANG ZHENYUAN BIOTECH CO., LTD., Shaoxing (CN); Tianjin University of Science and Technology, Tianjin (CN)

( * ) Notice: Subject to any disclaimer, the term of this patent is extended or adjusted under 35 U.S.C. 154(b) by 20 days.

(21) Appl. No.: 17/351,369

(22) Filed: Jun. 18, 2021

(65) Prior Publication Data

US 2022/0403348 A1    Dec. 22, 2022

(51) Int. Cl.
| | | |
|---|---|---|
| C12N 9/10 | (2006.01) | |
| C12N 9/06 | (2006.01) | |
| C12P 13/24 | (2006.01) | |
| C07K 14/245 | (2006.01) | |

(52) U.S. Cl.
CPC .......... *C12N 9/1077* (2013.01); *C07K 14/245* (2013.01); *C12N 9/0016* (2013.01); *C12P 13/24* (2013.01); *C12Y 104/01003* (2013.01); *C12Y 204/02017* (2013.01)

(58) Field of Classification Search
None
See application file for complete search history.

(56) References Cited

FOREIGN PATENT DOCUMENTS

| | | | |
|---|---|---|---|
| CN | 110184230 A | * | 8/2019 |
| CN | 110184230 A | | 8/2019 |
| JP | 2001238556 A | | 9/2001 |

OTHER PUBLICATIONS

CN110184230A. Published Aug. 30, 2019. English machine translation. (Year: 2019).*
Accession BFX14891. Feb. 7, 2019 (Year: 2019).*
Chica et al. Curr Opin Biotechnol. Aug. 2005;16(4):378-84. (Year: 2005).*
Singh et al. Curr Protein Pept Sci. 2017, 18, 1-11 (Year: 2017).*
Kizer et al. Appl Environ Microbiol. May 2008;74(10):3229-41. (Year: 2008).*
Prather et al. Curr Opin Biotechnol. Oct. 2008;19(5):468-74. (Year: 2008).*
Heyun Wu, et al., Highly Efficient Production of L-Histidine from Glucose by Metabolically Engineered *Escherichia coli*, ACS Synth. Biol., 2020, pp. 1813-1822, 9.
Yifan Li, et al., Metabolic engineering of *Escherichia coli* using CRISPR-Cas9 meditated genome editing, Metabolic Engineering, 2015, pp. 13-21, 31.
Robert K. Kulis-Horn, et al., Corynebacterium glutamicum ATP-phosphoribosyl transferases suitable for L-histidine production—Strategies for the elimination of feedback inhibition, Journal of Biotechnology, 2015, pp. 26-37, 206.
Shi Ting, Study on the relationship between rocG gene and nitrogen metabolism of Bacillus subtilis, 2011, pp. 1-64.

* cited by examiner

*Primary Examiner* — Christian L Fronda
(74) *Attorney, Agent, or Firm* — Bayramoglu Law Offices LLC

(57) ABSTRACT

A genetically engineered bacterium includes a genome of the *Eschericia coli* and a mutant encoding gene hisG* of a *Corynebacterium glutamicum* ATP phosphoribosyl transferase HisG on the genome, and the gene hisG* is strongly expressed to enhance activity of a key enzyme HisG for histidine synthesis. The gene hisG* has a nucleotide sequence as shown in SEQ ID NO: 1; a copy number of histidine operon genes hisDBCHAFI of the *Eschericia coli* is further increased on the genome to enhance a terminal synthetic route of histidine; an encoding gene lysE from an arginine/lysine transportprotein of the *Corynebacterium glutamicum* is further integrated to the genome and strongly expressed to promote the intracellular histidine secrete to the extracellular space; and an encoding gene rocG of glutamate dehydrogenase of *Bacillus subtilis* is further integrated to the genome and strongly expressed to promote generation of histidine.

12 Claims, 5 Drawing Sheets

Specification includes a Sequence Listing.

US 11,692,178 B2

GENETICALLY ENGINEERED BACTERIUM FOR PRODUCING L-HISTIDINE AND USE THEREOF

SEQUENCE LISTING

The instant application contains a Sequence Listing which has been submitted in ASCII format via EFS-Web and is hereby incorporated by reference in its entirety. Said ASCII copy is named GBRSMJ018_Sequence Listing.txt, created on Jun. 11, 2021 and is 12,193 bytes in size.

TECHNICAL FIELD

The present disclosure belongs to the technical field of genetic engineering, and in particular relates to a genetically engineered bacterium for producing L-histidine, a construction method and a use thereof.

BACKGROUND

L-histidine (hereinafter referred to as histidine) is an important functional amino acid taking part in various physiological and biochemical processes, such as body development, oxidation resistance and immunoregulation. Histidine, primarily applied to food, feed and medicine industries, can be used as a nutrient reinforcing agent and a feed additive, and can be used for producing amino acid infusion and comprehensive amino acid preparations, which have auxiliary therapy effect in diseases such as heart disease, anemia and gastrointestinal ulcer, thus histidine has very high economical and social value.

At present, histidine is primarily produced by the method of extracting from protein hydrolysate. But the method is high in loss ratio, corrodes equipment severely and is high in separation cost, therefore the method is not the optimum histidine production method. The microbiological fermentation method for producing histidine is low in material cost, environmental-friendly, easy to operate, short in period and suitable for industrial production, which has become a hot spot in production research of histidine at present. The bottleneck of producing histidine by the microbiological fermentation method lies in the lack of strains for efficiently produce histidine. This is mainly because of long biological synthetic route of histidine, severe and complex feedback regulation, and a coordinated supply of various precursors are required, especially a large supply of energy, which leads the thalli difficult to accumulate histidine in a large scale. In order to obtain production strains for producing histidine with a high yield, researches modify strains belonging to different species and achieve a series of results by applying various technical means, including conventional mutation screening, genetic engineering, metabolic engineering and the like. Although the technical means for researches are different, the strategy of the means is generally as follows: relieving feedback inhibition to a histidine synthetic route; enhancing the synthetic route of histidine; increasing supply of the precursors; blocking the metabolic pathway of histidine; and promoting extracellular secretion of histidine, etc.

The strain with the highest fermentation level of histidine reported at present is *E. coli* WHY3 (CN 110184230A). By taking *E. coli* W311 as an original strain, the strain is constructed from three aspects: relieving feedback regulation of histidine synthesis, enhancing the histidine synthetic route and promoting extracellular secretion of histidine. After fermentation for 40-50 hours in a 5 L fermentation tank, 40-55 g/L of histidine can be produced, the average production intensity is 1.0-1.5 g/(L*h) and the conversion ratio is 0.18-0.22 g histidine/g glucose. However, there is still a huge room for improvement of the output and conversation ratio of histidine.

SUMMARY

The present disclosure aims to provide a method for improving fermentation output of histidine and a new histidine fermentation production strain.

A technical scheme of the present disclosure outlined below:

the present disclosure provides a genetically engineered bacterium *E. coli* WHY3-1 for producing L-histidine with a high yield. The genetically engineered bacterium is a genome of the *Eschericia coli*, wherein the genome of the *Eschericia coli* is integrated with a mutant-encoding gene hisG*, having a nucleotide sequence as shown in SEQ ID NO: 1, of a corynebacterium glutamicum ATP phosphoribosyl transferase HisG and drives the same to express strongly to enhance activity of the HisG, a key enzyme for histidine synthesis; an expression of histidine operon genes hisDBCHAFI of the *Eschericia coli* is further enhanced on the genome to enhance a terminal synthetic route of histidine; an encoding gene lysE from an arginine/lysine transportprotein of the corynebacterium glutamicum is further integrated to the genome and is driven to strongly expressed to promote the intracellular histidine secrete to the extracellular space; and an encoding gene rocG of glutamate dehydrogenase of *Bacillus subtilis* is further integrated to the genome and is driven to strongly express to promote generation of histidine.

In at least one embodiment, the *Eschericia coli* is *E. coli* W3110.

In some embodiments, the histidine operon genes hisDBCHAFI include seven genes: hisD, hisB, hisC, hisH, hisA, hisF and hisI, such that the copy numbers of the seven genes on the genome of the *Eschericia coli* are increased.

In at least one embodiment, the mutant encoding gene hisG* of the corynebacterium glutamicum ATP phosphoribosyl transferase HisG is integrated to at least two genetic locus on the genome and is initiated by a strong promoter.

In at least one embodiment, strong expression of an exogenous gene can be realized by constructing a strong promoter.

In at least one embodiment, the mutant encoding gene hisG* of the corynebacterium glutamicum ATP phosphoribosyl transferase HisG is integrated to the tdcD and ylbE genetic locus on the genome of the *Eschericia coli* and is initiated by a strong promoter $P_{trc}$.

In at least one embodiment, the encoding gene rocG of the glutamate dehydrogenase is integrated to the yjhE gene locus on the genome of the *Eschericia coli* and transcriptional expression of the encoding gene rocG is controlled by a strong promoter $P_{trc}$.

In at least one embodiment, the genetically engineered bacterium *E. coli* WHY3-1 is obtained by conducting directional transformation on *E. coli* W3110 by adopting a CRISPR/Cas9 mediated gene editing technology, the method specifically including the following steps:

(1) constructing a connecting fragment $P_{trc}$-hisG* of a promoter $P_{trc}$ and a gene hisG* having a nucleotide sequence as shown in SEQ ID NO: 1, and integrating the connecting fragment to a tdcD gene locus and a ylbE gene locus on a genome respectively;

(2) constructing a connecting fragment $P_{trc}$-hisD-hisC-hisB-hisH-hisA-hisF-hisI of the promoter $P_{trc}$ and the histidine operon genes of the *Eschericia coli*, and integrating the connecting fragment to a yghX gene locus on the genome by a segmented integration method;

(3) constructing a connecting fragment $P_{trc}$-lysE of the promoter $P_{trc}$ and a gene lysE from a *Corynebacterium glutamicum*, and integrating the connecting fragment to a yjiT gene locus on the genome; and (4) constructing a connecting fragment $P_{trc}$-rocG of the promoter $P_{trc}$ and an encoding gene rocG of glutamate dehydrogenase from *Bacillus subtilis*, and integrating the connecting fragment to a yjhE gene locus on the genome.

The present disclosure further provides a method for preparing L-histidine, the method being to culture the genetically engineered bacterium under a suitable condition and collect histidine from a culture of the genetically engineered bacterium.

Beneficial effects:

At present, methods for improving the output of histidine are mainly focused on relieving feedback inhibition to a histidine synthetic route; enhancing the synthetic route of histidine; increasing supply of the precursors; blocking a metabolic pathway of histidine; and promoting extracellular secretion of histidine and the like. By introducing glutamate dehydrogenase of *Bacillus subtilis* into a histidine producing strain for the first time, a reaction of catalyzing α-ketoglutaric acid by the dehydrogenase of *Bacillus subtilis* to generate glutamic acid can mediate regeneration of glutamic acid and NAD+ simultaneously by taking NADH as a coenzyme, while glutamic acid and NAD+ are an ammonia donor and the coenzyme in the histidine synthetic process respectively, and thereby, the production efficiency of histidine is further improved. WHY3-1 is used for producing histidine by the fermentation method. Fermented for 36-48 hours in a 5L fermentation tank, 50-65 g/L of histidine can be produced. The average production intensity is 1.5-2.0 g/(L*h), the maximum value being 2.5 g/(L*h) and the conversion ratio is 0.2-0.24 g histidine/g glucose.

DETAILED DESCRIPTION OF THE EMBODIMENTS

The present disclosure is described below through specific embodiments. Unless otherwise specified, the technical means used in the present disclosure are all methods known to those skilled in the art. In addition, the embodiments should be understood as illustrative, rather than limiting the scope of the disclosure, which is only limited by the scope of the claims. For those skilled in the art, without departing from the spirit and scope of the present disclosure, various changes or modifications to the material composition and amount used in these embodiments also belong to the protection scope of the present disclosure.

Without public definition in the prior art and specific description, percent "%" in the embodiments below means percent by volume. Percent "% (m/v)" of a solution means gram of a solute in a 100 mL solution.

Embodiment 1

Construction of the strain *E. coli* WHY3-1

1. Gene Editing Method

Figure 1A:
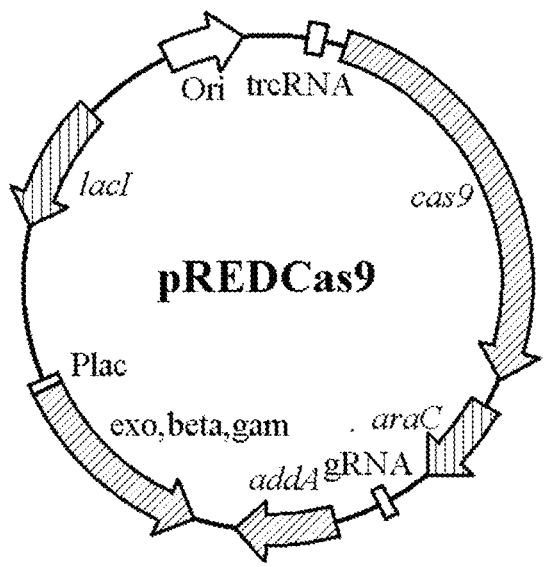
FIG. 1A is a pREDCas9 plasmid profile.
Figure 1B:
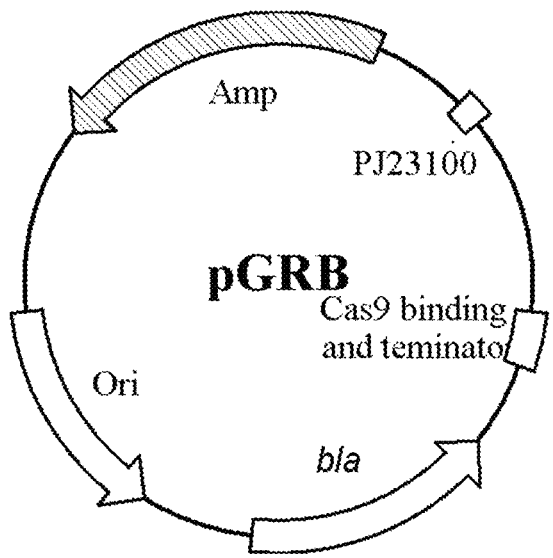
FIG. 1B is a pGRB plasmid profile.

The gene editing method adopted in the present disclosure was carried out with reference to literature (Li Y, Lin Z, Huang C, et al. Metabolic engineering of *Eschericia coli* using CRISPR—Cas9 meditated genome editing. Metabolic engineering, 2015, 31: 13-21.), the two plasmid profiles used by the method are shown in the FIGS. 1A-1B, wherein, pREDCas9 carried an eliminating system of a gRNA expression plasmid pGRB, a Red recombination system of a X, and a Cas9 protein expression system, spectinomycin resistance (the working concentration was 100 mg/L), culture was conducted at 32° C.; pGRB, taking pUC18 as a framework, included a promoter J23100, a gRNA-Cas9 binding region sequence and a terminator sequence, ampicillin resistance (the working concentration was 100 mg/L), and culture was conducted at 37° C.

The method includes the following specific steps:

1.1 pGRB Plasmid Construction

The construction of plasmid pGRB aims to transcribe corresponding gRNA to form a complex with a Cas9 protein, and recognize a targeted gene target site is recognized by base pairing and PAM, so as to realize double chain breaking of a target DNA. The pGRB plasmid was constructed by adopting a method of recombining a DNA fragment containing a target sequence and a linear carrier fragment.

1.1.1 Target Sequence Design

A target sequence (PAM:5'-NGG-3') was designed by using CRISPR RGEN Tools.

1.1.2 Preparation of the DNA Fragment Containing the Target Sequence

Designing a primer: 5'-linear carrier terminal sequence (15 bp)-restriction enzyme cutting site-target sequence(excluding PAM sequence)-linear carrier terminal sequence(15 bp)-3' and a reverse complementary primer thereof were used for preparing the DNA fragment containing the target sequence by annealing of a single-strand DNA. A reaction condition: initial denaturation at 95° C. for 5 min; and annealing at 30-50° C. for 1 min. An annealing system is as follows:

Annealing System

| Reaction system | Volume (20 μL) |
|---|---|
| Primer (10 μmol/L) | 10 μL |
| Reverse complementary primer (10 μmol/L) | 10 μL |

1.1.3 Preparation of a Linear Carrier

The carrier was linearized by way of reverse PCR amplification.

1.1.4 Recombination Reaction

A recombination system is shown in a table below. All used recombinases were ClonExpress® II One Step Cloning Kit serial enzymes, and a recombining condition was 37° C. for 30 min.

Recombination System

| Reaction system | Volume (20 μL) |
|---|---|
| 5*CE II Buffer | 4 μL |
| Linearized cloning vector | 1 μL |
| Insert fragment cloning vector | 1 μL |
| Exnase ® II | 2 μL |
| ddH2O | 12 μL |

1.1.5 Transformation of Plasmid

10 μL of a reaction liquid was taken and added into 100 μL, of DH5α competent cell, was then subjected to an ice-bath for 20 min after being mixed uniformly slightly, heat shock was conducted for 45-90 s at 42° C., the ice-bath was then conducted immediately for 2-3 min, and 900 μL of SOC was added for revival at 37° C. for 1 h. Centrifugation was conducted for 2 min at 8000 rpm, part of supernatant was abandoned, about 200 μL of the supernatant was reserved to resuspend thalli and then coated on a panel containing 100 mg/L of ampicillin, the panel was placed reversely and culture was performed overnight at 37° C. After a single colony grew on the panel, PCR authentication of the colony was performed and positive recons were selected.

1.1.6 Cloning Authentication

A PCR positive bacterial colony was inoculated to the LB culture medium containing 100 mg/L of ampicillin, was cultured overnight and preserved, and then the plasmid was extracted for digestion authentication.

1.2 Preparation of a Recombinant DNA Fragment

A recombinant fragment for knockout was comprised of upstream and downstream homologous arms (upstream homologous arm-downstream homologous arm) of gene to be knocked out, and a recombinant fragment for integration was comprised of upstream and downstream homologous arms on the integration site and gene fragment to be integrated (upstream homologous arm-target gene-downstream homologous arm). By using primer design software primer 5, upstream and downstream homologous arm primers (an amplification length was about 400-500 bp) was designed by taking upstream and downstream sequences of the gene to be knocked out or the site to be integrated as a template; and an amplification primer of the integrated gene was designed by taking the gene to be integrated as a template. After amplifying the upstream and downstream homologous arms and the target gene fragment by a PCR method, the recombinant fragment was prepared through overlapped PCR. A PCR system and method is as shown in the table below:

PCR Amplification System

| Components | Volume (50 μL) |
|---|---|
| DNA template | 1 μL |
| Upstream primer (10 μmol/L) | 1 μL |
| Downstream primer (10 μmol/L) | 1 μL |
| dNTP mixture(10 mmol/L) | 4 μL |
| 5*Buffer | 10 μL |
| HS enzyme (5 U/μL) | 0.5 μL |
| ddH2O | 32.5 μL |

The overlapped PCR system is as shown in the table below:

Overlapped PCR amplification system

| Components | Volume (50 μL) |
|---|---|
| Template | 2 μL |
| Upstream primer of upstream homologous arm (10 μmol/L) | 1 μL |
| Downstream primer of downstream homologous arm (10 μmol/L) | 1 μL |
| dNTP mixture(10 mmol/L) | 4 μL |
| 5*Buffer | 10 μL |
| HS enzyme (5 U/μL) | 0.5 μL |
| ddH2O | 31.5 μL |

Note:
the template was comprised of the amplification fragments of upstream and downstream homologous arms and the target gene at equal mole, and the total amount did not exceed 10 mg.

PCR reaction condition (Takara Bio PrimeSTAR HS enzyme): initial denaturation was conducted for 5 min at 95° C.; then 30 cycles were conducted: denaturation for 10 min at 98° C., annealing for 15 s ((Tm-3/5)° C.), and extension at 72° C. (the enzyme activity extends about 1 kb every 1 min); and extension was further conducted for 10 min at 72° C.; and was kept at 4° C.

1.3 Transformation of Plasmid and Recombinant DNA Fragment 1.3.1 Transformation of pREDCas9

The pREDCas9 plasmid was electrotransformed to an electrotransformed competence of W3110 by an electrotransformation method, the thalli was coated on the LB panel containing spectinomycin after revival culture, and was cultured overnight at 32° C. The single colony grew on a resistant panel was conducted colony PCR by authenticating primer, and the positive recons were selected.

1.3.2 Electrotransformed Competence Preparation of Target Strain Containing pREDCas9

When it was cultured to $OD_{600}$=0.1-0.2 at 32° C., 0.1 M of IPTG (enabling the final concentration thereof to be 0.1 mM) was added, and culture was further conducted till $OD_{600}$=0.6-0.7 to prepare competence. The purpose of adding IPTG was to induce expression of the recombinase on the pREDCas9 plasmid. A culture medium needed for preparing competence and a preparation process were operated with reference to a conventional standard.

1.3.3 Transformation of pGRB and Recombinant DNA Fragment pGRB and the donor DNA fragment were electrotransformed to the electrotransformed competent cell containing the pREDCas9 simultaneously. The electrotransformed thalli after revival culture was coated on the LB panel containing ampicillin and spectinomycin and was cultured overnight at 32° C. Colony PCR authentication was conducted by using the upstream primer of the upstream homologous arm and the downstream primer of the downstream homologous arm, or a designed special authenticating primer, and the positive recons were selected and the bacterium was preserved.

1.4 Elimination of Plasmid

1.4.1 Elimination of pGRB

The positive recons were placed in the LB culture medium containing 0.2% arabinose and was cultured overnight, then was coated on the LB panel containing spectinomycin resistance after being diluted properly and was cultured overnight at 32° C. The sample points on the LB panel containing ampicillin and spectinomycin resistance were contrasted, and the single-colonies not growing on the panel containing ampicillin and growing on the panel containing spectinomycin were selected for bacterium preservation.

1.4.2 Elimination of pREDCas9 Plasmid

The positive recons were transferred to the resistance-free LB liquid medium and was cultured overnight at 42° C., then was coated on the resistance-free LB panel after being diluted properly and was cultured overnight at 37° C. The sample points on the LB panel containing spectinomycin and the resistance-free LB panel were contrasted, and the single-colonies not growing on the panel containing spectinomycin resistance and growing on the resistance-free panel were selected for bacterium preservation.

2. All primers in the strain construction process are as shown in the table below:

| Primers | SEQ ID NO: | Sequences (5'-3') |
|---|---|---|
| UP-tdcD-S | 2 | TATTCAAAACAGAAAAACCGTCAGT |
| UP-tdcD-A | 3 | AATTGTTATCCGCTCACAATTCCACACATTATACGAGCCGGATGATTAATTGTCAAGGCAAATCGCGAAGAAGTACAG |
| hisG*-S | 4 | TCCGGCTCGTATAATGTGTGGAATTGTGAGCGGATAACAATTTCACACAGGAAACAGACCATGTTGAAAATCGCTGTCCCA |
| hisG*-A | 5 | CACCGACAAACAACAGATAAAACGAAAGGCCCAGTCTTTCGACTGAGCCTTTCGTTTTATTTGCTAGTTCTGCGCGTGCAAAA |
| DN-tdcD-S | 6 | AAAGACTGGGCCTTTCGTTTTATCTGTTGTTTGTCGGTGAACGCTCTCCTGAGTAGGACAAATTGAATAATCGCTCTAACTCCTGTG |
| DN-tdcD-A | 7 | CGCCCTGGTTATGGGTTTT |
| UP-ylbE-S | 8 | ACCCAACCTTACGCAACCAG |
| UP-ylbE-A | 9 | AATTGTTATCCGCTCACAATTCCACACATTATACGAGCCGGATGATTAATTGTCAATTGTTCGATAACCGCAGCAT |
| DK-ylbE-S | 10 | AAAGACTGGGCCTTTCGTTTTATCTGTTGTTTGTCGGTGAACGCTCTCCTGAGTAGGACAAATCGCTGGCGTGCTTTGAA |
| DN-ylbE-A | 11 | GGCGTAACTCAGCAGGCAG |
| UP-yghX-S | 12 | TTTGTTCTCTTCGACCTGATGAC |
| UP-yghX-A | 13 | AATTGTTATCCGCTCACAATTCCACACATTATACGAGCCGGATGATTAATTGTCAACTGTTCTACGTTGCGCTTTTT |
| hisD-S | 14 | TCCGGCTCGTATAATGTGTGGAATTGTGAGCGGATAACAATTTCACACAGGAAACAGACCATGAGCTTTAACACAATCATTGACT |
| hisD-A | 15 | GCCCCAAGGGGTTATGCTAGCCTACAAATTGAGTTATGTTCATTTAAATATGATGTTGTTCAGTCATGCTTGCTCCTTAAGGG |
| DN-yghX-S1 | 16 | CTGAACAACATCATATTTAAATGAACATAACTCAATTTGTAGGCTAGCATAACCCCTTGGGGCGTCATAGTAATCCAGCAACTCTTGTG |

-continued

| Primers | SEQ ID NO: | Sequences (5'-3') |
|---|---|---|
| DN-yghX-A | 17 | GAGCAGGTATTTACGTGAACCG |
| UP-hisCB-S | 18 | ATTTCGTGGCTTCTGATTTGCT |
| UP-hisCB-A | 19 | AGTTGCTGGATTACTATGACCCTAGAAGAAATCAACCAG CGCATCAGAAAGTCTCCTGTGCATTTACAGCACTCCTTTC GACGAG |
| DK-yghX-S2 | 20 | ATGCACAGGAGACTTTCTGATGCGCTGGTTGATTTCTTCT AGGGTCATAGTAATCCAGCAACT GTCATAGTAATCCAGCAACTCTTGTG |
| UP-hisHAFI-S | 21 | GTGACCGTTACGCTCACGTAGT |
| UP-hisHAFI-A | 22 | CACCGACAAACAACAGATAAAACGAAAGGCCCAGTCTT TCGACTGAGCCTTTCGTTTTATTTGTCACTGATGCCGTTT ACGCA |
| DN-yghX-S3 | 23 | AAAGACTGGGCCTTTCGTTTTATCTGTTGTTTGTCGGTGA ACGCTCTCCTGAGTAGGACAAAT GTCATAGTAATCCAGCAACTCTTGTG |
| UP-yjiT-S | 24 | AATAGTTGTTGCCGCCTGAGT |
| UP-yjiT-A | 25 | AATTGTTATCCGCTCACAATTCCACACATTATACGAGCC GGATGATTAATTGTCAAAAAACAGGCAGCAAAGTCCC |
| lysE-S | 26 | TCCGGCTCGTATAATGTGTGGAATTGTGAGCGGATAACA ATTTCACACAGGAAACAGACCATGGTGATCATGGAAATC TTCATTA |
| lysE-A | 27 | CACCGACAAACAACAGATAAAACGAAAGGCCCAGTCTT TCGACTGAGCCTTTCGTTTTATTTGCTAACCCATCAACAT CAGTTTGATG |
| DN-yjiT-S | 28 | AAAGACTGGGCCTTTCGTTTTATCTGTTGTTTGTCGGTGA ACGCTCTCCTGAGTAGGACAAATAAGCACTACCTGTGAA GGGATGT |
| DN-yjiT-A | 29 | CAGGGCTTCCACAGTCACAAT |
| gRNA-tdcDS | 30 | AGTCCTAGGTATAATACTAGTAAAAGAGATGAATGAATT TCGTTTTAGAGCTAGAA |
| gRNA-tdcD-X | 31 | TTCTAGCTCTAAAACGAAATTCATTCATCTCTTTTACTAG TATTATACCTAGGACT |
| gRNA-ylbE-S | 32 | AGTCCTAGGTATAATACTAGTACACTGGCTGGATGTGCA ACGTTTTAGAGCTAGAA |
| gRNA-ylbE-A | 33 | TTCTAGCTCTAAAACGTTGCACATCCAGCCAGTGTACTA GTATTATACCTAGGACT |
| gRNA-yghX-S | 34 | AGTCCTAGGTATAATACTAGTGGTGCCTGACGACCATAA AAGTTTTAGAGCTAGAA |
| gRNA-yghX-A | 35 | TTCTAGCTCTAAAACTTTTATGGTCGTCAGGCACCACTA GTATTATACCTAGGACT |
| gRNA-his1-S | 36 | AGTCCTAGGTATAATACTAGTATGAACATAACTCAATTT GTGTTTTAGAGCTAGAA |
| gRNA-his1-A | 37 | TTCTAGCTCTAAAACACAAATTGAGTTATGTTCATACTA GTATTATACCTAGGACT |
| gRNA-his2-S | 38 | AGTCCTAGGTATAATACTAGTTGCGCTGGTTGATTTCTTC TGTTTTAGAGCTAGAA |
| gRNA-his2-A | 39 | TTCTAGCTCTAAAACAGAAGAAATCAACCAGCGCAACTA GTATTATACCTAGGACT |
| gRNA-yjiT-S | 40 | AGTCCTAGGTATAATACTAGTAGGGATTATGAACGGCAA TGGTTTTAGAGCTAGAA |

-continued

| Primers | SEQ ID NO: | Sequences (5'-3') |
|---|---|---|
| gRNA-yjiT-A | 41 | TTCTAGCTCTAAAACCATTGCCGTTCATAATCCCTACTAG TATTATACCTAGGACT |
| UP-yjhE-S | 42 | GTCAGGCACTGGCGAAAGAT |
| UP-yjhE-A | 43 | AATTGTTATCCGCTCACAATTCCACACATTATACGAGCC GGATGATTAATTGTCAACGCAAGCCATAAACCCACA |
| rocG-S | 44 | TCCGGCTCGTATAATGTGTGGAATTGTGAGCGGATAACA ATTTCACACAGGAAACAGACCATGTCAGCAAAGCAAGT CTCGA |
| rocG-A | 45 | CACCGACAAACAACAGATAAAACGAAAGGCCCAGTCTT TCGACTGAGCCTTTCGTTTTATTTGTTAGACCCATCCGCG GAAA |
| DN-yjhE-S | 46 | CTGGGCCTTTCGTTTTATCTGTTGTTTGTCGGTGAACGCT CTCCTGAGTAGGACAAATTTCCGACATCGAAATGCGT |
| DN-yjhE-A | 47 | AGGCGTTGTTGTGGCAGATT |

Figure 2:
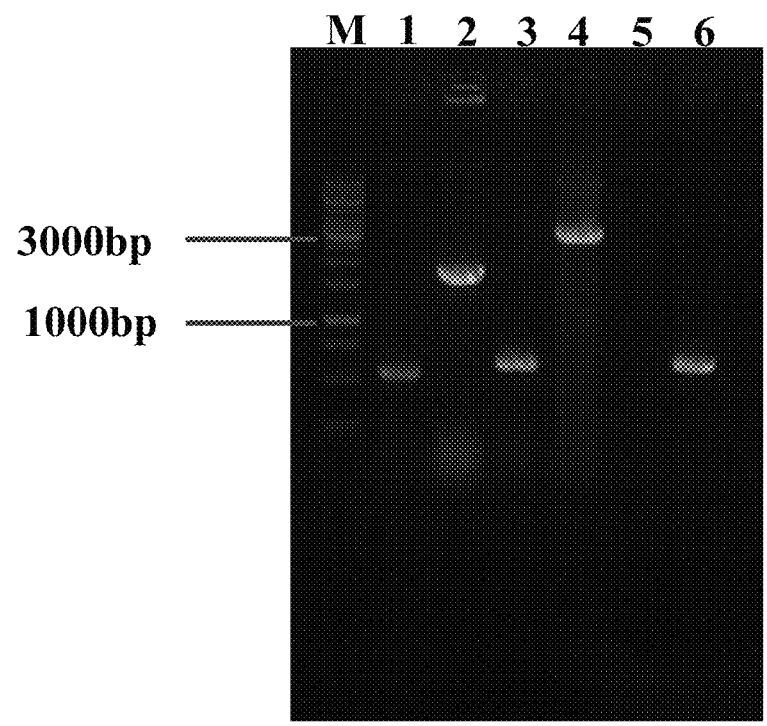
FIG. 2 is an integrating fragment construction and verification electrophoretogram when hisG* is integrated to the tdcD gene locus, wherein, M: 1 kb DNA marker; 1: upstream homologous arm; 2: hisG* gene fragment; 3: downstream homologous arm; 4: overlapped fragment; 5: original bacterium contrast; 6: authenticating fragment for positive bacterium.

3. Specific Process of Strain Construction 3.1 Relieving a Feedback Inhibition of HisG and making it Strongly Expressed 3.1.1 Integrating $P_{trc}$-hisG* to the tdcD gene locus By taking a genome of E. coli W3110 (ATCC 27325) as a template, the upstream homologous arm primers (UP-tdcD-S and UP-tdcD-A) and downstream homologous arm primers (DN-tdcD-S and DN-tdcD-A) were designed according to upstream and downstream sequences of the tdcD gene of the genome, and PCR amplification was conducted on the upstream and downstream homologous arm fragments; the primers (hisG*-S and hisG*-A) were designed according to the hisG* gene (the nucleotide sequence is as shown in SEQ ID NO: 1) and then the hisG* gene fragment was amplified. The promoter $P_{trc}$ was designed in the downstream primer of the upstream homologous arm and the upstream primer of the hisG* gene. An integrated fragment (the upstream homologous arm-$P_{trc}$-hisG*-downstream homologous arm) of the hisG* gene was obtained by performing overlapped PCR method on the above fragments, and the DNA fragment containing a target sequence used for constructing pGRB-tdcD was prepared by annealing the primers gRNA-tdcD-S and gRNA-tdcD-A. The preparation of competent cell of E. coli W3110 was operated according to the method as shown in 1.3 and 1.4, the strain E. coli WHY1-1 was finally obtained. The electrophoretogram of construction of the $P_{trc}$-hisG* integrated fragment and PCR verification of the positive strain is as shown in the FIG. 2. Wherein, the length of the upstream homologous arm is 496 bp, the length of the amplified hisG* gene fragment shall be 627 bp, the length of the downstream homologous arm is 1902 bp, and the total length of the integrated fragment is 3024 bp, when PCR verification was conducted by using the authenticating primers, the length of the PCR amplification fragment of the positive strain is 627 bp, and the original strain is free of band.

3.1.2 Integrating $P_{trc}$-hisG* to the ylbE Gene Locus

Figure 3:
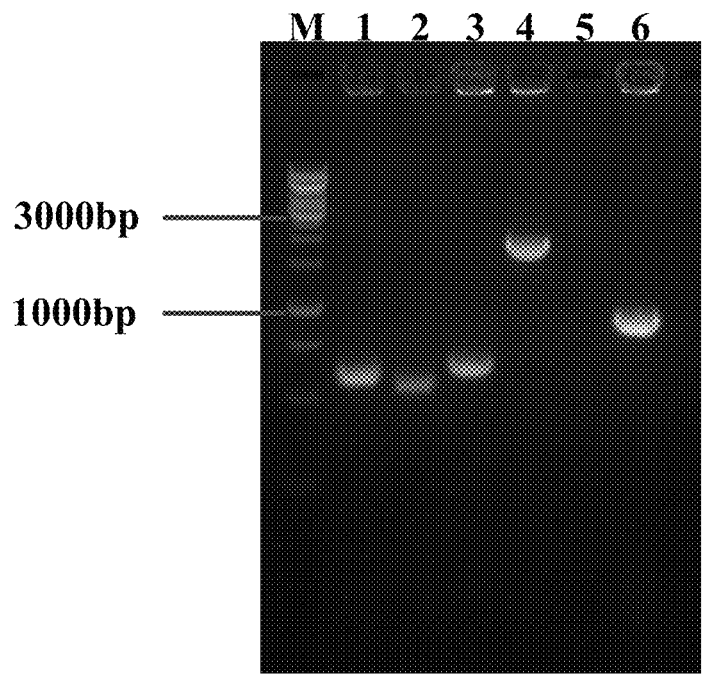
FIG. 3 is an integrating fragment construction and verification electrophoretogram when hisG* is integrated to the ylbE gene locus, wherein, M: 1 kb DNA marker; 1: upstream homologous arm; 2: hisG* gene fragment; 3: downstream homologous arm; 4: overlapped fragment; 5: original bacterium contrast; 6: authenticating fragment for positive bacterium.

By taking a genome of E. coli W3110 (ATCC 27325) as a template, the upstream homologous arm primers (UP-ylbE-S and UP-ylbE-A) and downstream homologous arm primers (DN-ylbE-S and DN-ylbE-A) were designed according to upstream and downstream sequences of the ylbE gene of the genome, and PCR amplification was conducted on the upstream and downstream homologous arm fragments; and the hisG* gene fragment was amplified by using the primers (hisG *-S and hisG*-A). The integrated fragment (the upstream homologous arm-$P_{trc}$-hisG*-downstream homologous arm) of the hisG* gene was obtained by performing overlapped PCR method on the above fragments, and the DNA fragment containing a target sequence used for constructing pGRB-ylbE was prepared by annealing the primers gRNA-ylbE-S and gRNA-ylbE-A. The preparation of competent cell of E. coli WHY1-1 was operated according to the method as shown in 1.3 and 1.4, the strain E. coli WHY1-2 was finally obtained. The electrophoretogram of constructiion of the $P_{trc}$-hisG* integrated fragment and PCR verification of the positive strain is as shown in the FIG. 3. Wherein, the length of the upstream homologous arm is 601 bp, the length of the amplified hisG* gene fragment is 627 bp, the length of the downstream homologous arm is 547 bp, and the total length of the integrated fragment is 1815 bp, when PCR verification was conducted by using the authenticating primers, the length of the PCR amplification fragment of the positive strain is 903 bp, and the original strain is free of band.

3.2 Integrating the Histidine Operon Gene of E. coli W3110 to the yghX Gene Locus In the present disclosure, the histidine operon genes (hisDBCHAFI, including seven genes: hisD, hisB, hisC, hisH, hisA, hisF and hisI) in E. coli W3110 were successively integrated to a pseudogene yghX locus on the genome of E. coli WHY1-2 in sequence, and the promoter $P_{trc}$ initiates transcriptional expression of the operon to construct a strain E. coli HIS3-3.

Integration of the histidine operon genes was divided into three segments.

3.2.1 Integration of $P_{trc}$-hisD

Figure 4:
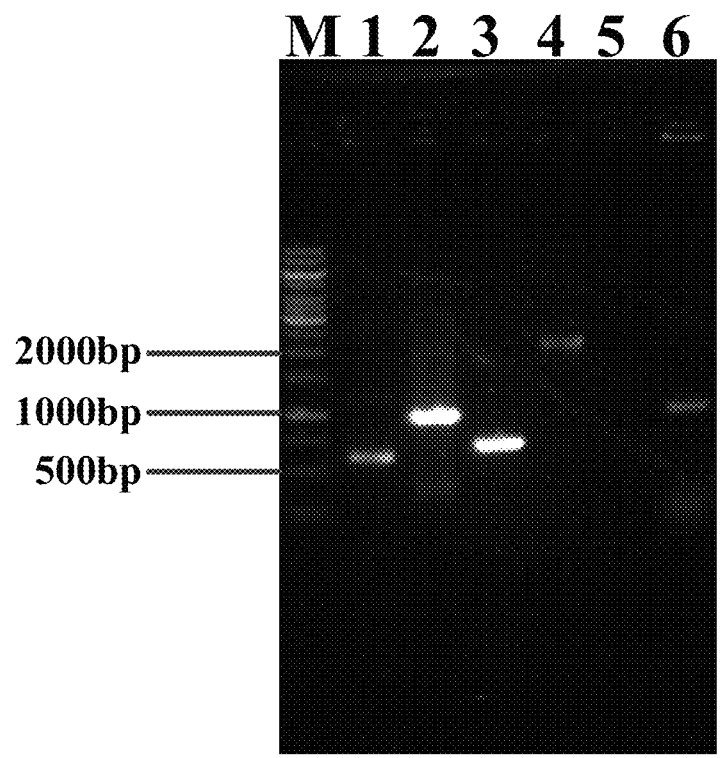
FIG. 4 is a hisD integrating fragment construction and verification electrophoretogram, wherein, M: 1 kb DNA marker; 1: upstream homologous arm; 2: hisG* gene fragment; 3: downstream homologous arm; 4: overlapped fragment; 5: original bacterium contrast; 6: authenticating fragment for positive bacterium.

By taking a genome of E. coli W3110(ATCC 27325) as a template, the upstream homologous arm primers (UP-yghX-S and UP-yghX-A) and downstream homologous arm primers (DN-yghX-S1 and N-yghX-A) were designed according to upstream and downstream sequences of the yghX gene of the genome, and PCR amplification was conducted on the upstream and downstream homologous arm fragments; the primers (hisD-S and hisD-A) were designed according to the hisD gene sequence and the hisD gene fragment was PCR amplified; and the promoter Pfrc was designed in the downstream primer of the upstream homologous arm and the upstream primer of the hisD gene. The above fragments were fused by the overlapped PCR method to obtain the integrated fragment (the upstream homologous arm-$P_{trc}$-hisD-downstream homologous arm) of the $P_{trc}$-hisD gene, the DNA fragment containing a target sequence used for constructing pGRB-yghX was prepared by annealing the primers gRNA-yghX-S and gRNA-yghX-A. The competent cell of E. coli WHY1-2 was according to the method as shown in 1.3 and 1.4, and the strain E. coli WHY2-1 was finally obtained. In the $P_{trc}$-hisD fragment integrating process, the electrophoretogram of construction of the integrated fragment and PCR verification of the positive strain is as shown in the FIG. 4. Wherein, the length of the upstream homologous arm is 602 bp, the length of the amplified hisD gene fragment is 1305 bp, the length of the downstream homologous arm is 561 bp, and the length of the overlapped fragment is 2542 bp, when PCR verification was conducted by using the authenticating primers, the length of the fragment amplified by the positive recons is 1208 bp, and the original strain is free of band.

3.2.2 Integration of hisB-hisC

Figure 5:
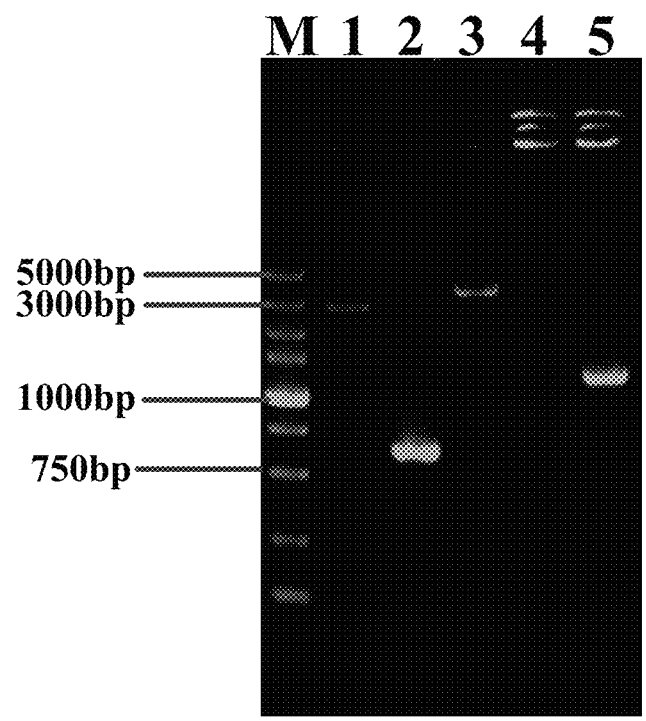
FIG. 5 is a hisC-hisB integrating fragment construction and verification electrophoretogram, wherein, M: 1 kb DNA marker; 1: hisC-upstream sequence-hisC-hisB fragment; 2: downstream homologous arm; 3: overlapped fragment; 4: original bacterium contrast; 5: authenticating fragment for positive bacterium.

By taking a genome of E. coli W3110 (ATCC 27325) as a template, the upstream homologous arm primers (UP-hisCB-S and UP-hisCB-A) were designed according to hisC-hisB and upstream sequences thereof, and PCR amplification was conducted on the upstream homologous arm fragment; by taking a genome of E. coli HIS3-1 as a template, the downstream homologous arm primers (DN-yghX-S2 and DN-yghX-A) were designed according to downstream sequences of the yghX gene of the genome, and PCR amplification was conducted on the downstream homologous arm fragment. The fragments were integrated by the overlapped PCR method to obtain the integrated fragment (upstream fragment of hisC-hisC-hisB-downstream homologous arm) of hisC-hisB. The DNA fragment containing the target sequence used for constructing pGRB-hisI was prepared by annealing the primers gRNA-his1-S and gRNA-his1-A. The competent cell of E. coli WHY2-1 was prepared according to the method as shown in 1.3 and 1.4, and the strain E. coli WHY2-2 was finally obtained. In the hisB-hisC fragment integrating process, the electrophoretogram of construction of the integrated fragment and PCR verification of the positive strain is as shown in the FIG. 5. Wherein, the total length of the upstream fragment of hisC-hisC-hisB is 2696 bp, the length of the downstream homologous arm is 561 bp, and the length of the overlapped fragment is 3317 bp, when PCR verification was conducted by using the authenticating primers, the length of the fragment amplified by the positive recons is 1118 bp, and the original strain is free of band.

3.2.3 Integration of hisH-hisA-hisF-hisI

Figure 6:
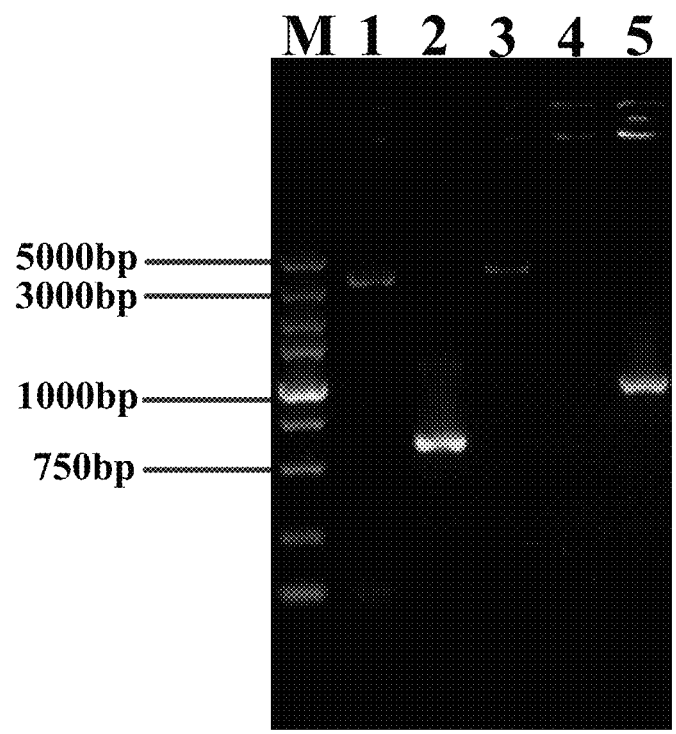
FIG. 6 is a hisH-hisA-hisF-hisI integrating fragment construction and verification electrophoretogram, wherein, M: 1 kb DNA marker; 1: hisH-upstream sequence-hisH-hisA-hisF-hisI fragment; 2: downstream homologous arm; 3: overlapped fragment; 4: original bacterium contrast; 5: authenticating fragment for positive bacterium.

By taking a genome of E. coli W3110 (ATCC 27325) as a template, the upstream homologous arm primers (UP-hisHAFI-S and UP-hisHAFI-A) were designed according to hisH-hisA-hisF-hisI and upstream sequences thereof, and PCR amplification was conducted on the upstream homologous arm fragment; by taking a genome of E. coli HIS3-2 as a template, the downstream homologous arm primers (DN-yghX-S3 and DN-yghX-A) were designed according to downstream sequences of the yghX gene of the genome, and PCR amplification was conducted on the downstream homologous arm fragment. The fragments were fused by the overlapped PCR method to obtain the integrated fragment (upstream fragment of hisH-hisH-hisA-hisF-hisI-downstream homologous arm) of hisH-hisA-hisF-hisI. The DNA fragment containing the target sequence used for constructing pGRB-his2 was prepared by annealing the primers gRNA-his2-S and gRNA-his2-A. The competent cell of E. coli WHY2-2 was prepared according to the method as shown in 1.3 and 1.4, and the strain E. coli WHY2-3 was finally obtained. In the integrating process of hisH-hisA-hisF-hisI, the electrophoretogram of contruction of the integrated fragment and PCR verification of the positive strain is as shown in the FIG. 6. The total length of the upstream fragment of hisH-hisH-hisA-hisF-hisI is 3265 bp, the length of the downstream homologous arm is 561 bp, and the length of the overlapped fragment is 3317 bp, when PCR verification was conducted by using the authenticating primers, the length of the fragment amplified by the positive recons is 1136 bp, and the original strain is free of band.

3.3 Integration of $P_{trc}$-lysE

Figure 7:
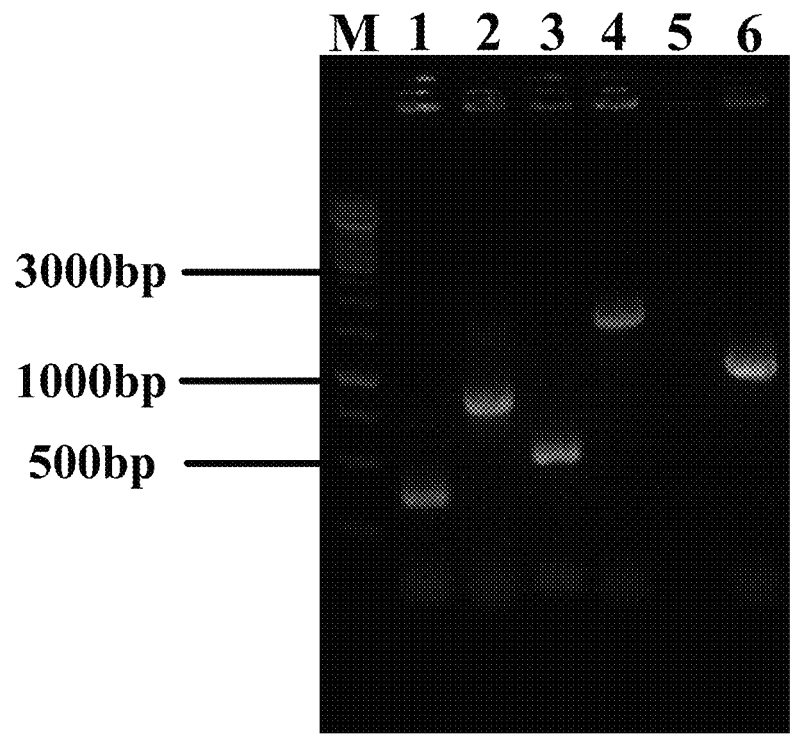
FIG. 7 is a $P_{trc}$-lysE integrating fragment construction and verification electrophoretogram, wherein, M: 1 kb DNA marker; 1: upstream homologous arm; 2: lysE gene fragment; 3: downstream homologous arm; 4: overlapped fragment; 5: original bacterium contrast; 6: authenticating fragment for positive bacterium.

By taking a genome of E. coli W3110 (ATCC ATCC27325) as a template, the upstream homologous arm primers (UP-yjiT-S and UP-yjiT-A) and the downstream homologous arm primers (DN-yjiT-S and DN-yjiT-A) were designed according to upstream and downstream sequences of the yjiT gene of the genome and PCR amplification was conducted on the upstream and downstream homologous arm fragments; by taking a genome of corynebacterium glutamicum (ATCC 13032) as a template, the primers (lysE-S and lysE-A) were designed according to the sequence of lysE (NCBI-GeneID: 1019244) gene and PCR amplification was conducted on the lysE fragment; and the promoter $P_{trc}$ was designed in the downstream primer of the upstream homologous arm and the upstream primer of the lysE gene. The fragments were fused by the overlapped PCR method to obtain the integrated fragment (the upstream homologous arm-$P_{trc}$-lysE-downstream homologous arm) of $P_{trc}$-lysE, and the DNA fragment containing a target sequence used for constructing pGRB-yjiT was prepared by annealing the primers gRNA-yjiT-S and gRNA-yjiT-A. The competent cell of E. coli WHY2-3 was prepared according to the method as shown in 1.3 and 1.4, and the strain E. coli WHY3 was finally obtained. In the $P_{trc}$-lysE fragment integrating process, the electrophoretogram of construction of the integrated fragment and PCR verification of the positive strain is as shown in the FIG. 7. Wherein, the length of the upstream homologous arm is 372 bp, the length of the lysE gene fragment is 834 bp, the length of the downstream homologous arm 530 bp, and the length of the overlapped fragment is 1655 bp, when PCR verification was conducted by using the authenticating primers, the length of the fragment amplified by the positive recon is 1429 bp, and the original strain is free of band.

3.4 Integration of $P_{trc}$-rocG

Figure 8:
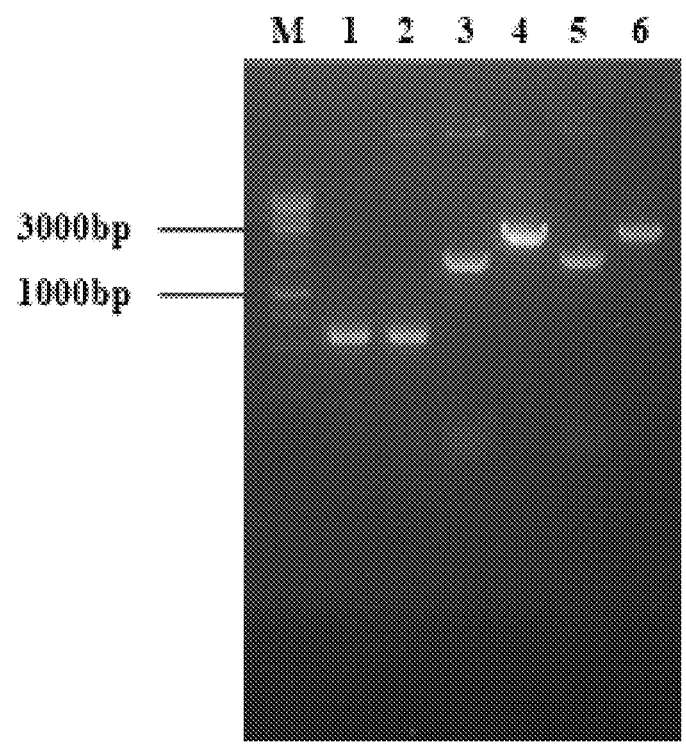
FIG. 8 is an integrating fragment construction and verification electrophoretogram when rocG is integrated to the yjhE gene locus, wherein, M: 1 kb DNA marker; 1: upstream homologous arm; 2: downstream homologous arm; 3: rocG gene fragment; 4: overlapped fragment; 5: original bacterium contrast; 6: authenticating fragment for positive bacterium.

By taking a genome of E. coli W3110 as a template, the upstream homologous arm primers (UP-yjhE-S and UP-yjhE-A) and the downstream homologous arm primers (DN-yjhE-S and DN-yjhE-A) were designed according to upstream and downstream sequences of the yjhE gene of the genome and PCR amplification was conducted on the upstream and downstream homologous arm fragments; by taking a genome of B. subtilis 168 as a template, the primers (rocG-S and rocG-A) were designed according to the sequence of rocG (NCBI-GeneID: 937066) gene and PCR amplification was conducted on the rocG fragment; and the promoter $P_{trc}$ was designed in the downstream primer of the upstream homologous arm and the upstream primer of the rocG gene. The fragments were fused by the overlapped PCR method to obtain the integrated fragment (the upstream homologous arm-P$_{trc}$-rocG-downstream homologous arm) of the P$_{trc}$-rocG gene, and the DNA fragment containing a target sequence used for constructing pGRB-yjhE was prepared by annealing the primers gRNA-yjhE-S and gRNA-yjhE-A. The competent cell of *E. coli* WHY3 was prepared according to the method as shown in 1.3 and 1.4, and the strain *E. coli* WHY3-1 was finally obtained. In the P$_{trc}$-rocG fragment integrating process, the electrophoretogram of construction of the integrated fragment and PCR verification of the positive strain is as shown in the FIG. 8. Wherein, the total length of the upstream homologous arm is 602 bp, the length of the rocG gene fragment is 1398 bp, the length of the downstream homologous arm 491 bp, and the length of the overlapped fragment is 2419 bp, when PCR verification was conducted by using the primers UP-yjhE-S and DN-yjhE-A, the length of the fragment amplified by the positive recons is 2419 bp, and the original strain is 1547 bp.

Embodiment 2

Fermentation production of the histidine by using the genetically engineered bacterium *E. coli* WHY3-1 is as follows:

(1) Adopting Shake-Flask Culture slant culture: a −80° C. preserved strain was taken and inoculated on an activating slant through streak inoculation, and was cultured for 12 h at 37° C., subculture was conducted once;

shake-flask seed culture: an annular slant seed was scratched by using an inoculating loop and was inoculated in a 500 mL triangular flask filled with 30 mL of culture medium, the triangular flask was sealed with nine-layered gauze, and culture was conducted for 6-8 h at 200 rpm under 37° C.;

shake-flask fermental culture: 10-15% of the seed solution was inoculated in the 500 mL triangular flask (the final volume was 30 mL) filled with a fermentation medium, the triangular flask was sealed with nine-layered gauze, shake culture was conducted at 37° C. under 200 r/min, pH was maintained at 7.0-7.2 by replenishing ammonia water in a fermenting process, and a 60% (m/v) glucose solution was replenished to maintain fermentation;

a slant culture medium was composed of 1-5 g/L of glucose, 5-10 g/L of peptone, 5-10 g/L of beef extract, 1-5 g/L of yeast powder, 1-2.5 g/L of NaCl, 20-25 g/L of agar and the balance water, wherein pH was 7.0-7.2;

a seed culture medium was composed of 15-30 g/L of glucose, 5-10 g/L of yeast extract, 5-10 g/L of peptone, 5-15 g/L of KH$_2$PO$_4$, 2-5 g/L of MgSO$_4$·7H$_2$O, 5-20 mg/L of FeSO$_4$·7H$_2$O, 5-20 mg/L of MnSO$_4$·HO, 1-3 mg/L of V$_{B1}$, 0.1-1 mg/L of V$_H$, two drops of a defoamer and the balance water, wherein pH was 7.0-7.2;

a fermentation medium was composed of 20-30 g/L of glucose, 2-5 g/L of yeast extract, 2-4 g/L of peptone, 1-3 g/L of KH$_2$PO4, 1-2 g/L of MgSO$_4$·7H$_2$O, 5-20 mg/L of FeSO$_4$·7H$_2$O, 5-20 mg/L of MnSO$_4$·7H$_2$O, 1-3 mg/L of V$_{B1}$, 1-3 mg/L of V$_{B2}$, 1-3 mg/L of V$_{B3}$, 1-3 mg/L of V$_{B5}$, 1-3 mg/L of V$_{B12}$, 1-3 mg/L of V$_H$ and the balance water, wherein pH was 7.0-7.2.

(2) or Adopting a Fermentation Tank for Culture slant activating culture: a ring of strain was scraped from a strain preservation tube of a refrigerator at −80° C., and uniformly coated on the activating slant, was cultured for 12-16 h at 37° C., and was then transferred to an eggplant-shaped flask to be further cultured for 12-16 h;

seed culture: a proper amount of sterile water was taken and added into the eggplant-shaped flask, a bacterium suspension was inoculated in the seed culture medium, the pH was stabilized at about 7.0, the temperature was constant at 37° C., the content of dissolved oxygen was between 25-35%, and the bacterium suspension was cultured till the OD$_{600}$ value of fermentation liquor reached 10-15;

the seed solution was inoculated into a fresh fermentation medium according to an inoculation amount of 15-20%, fermentation was started, pH was controlled stably at about 7.0 in the fermenting process, temperature was maintained at 37° C. and dissolved oxygen was maintained between 25-35%; after glucose in the fermentation medium was exhausted, a 80% (m/v) glucose solution was fed to maintain the glucose concentration in the fermentation medium at 0.1-5 g/L;

a slant culture medium was composed of 1-5 g/L of glucose, 5-10 g/L of peptone, 5-10 g/L of beef extract, 1-5 g/L of yeast powder, 1-2.5 g/L of NaCl, 20-25 g/L of agar and the balance water, wherein pH was 7.0-7.2;

a seed culture medium was composed of 15-30 g/L of glucose, 5-10 g/L of yeast extract, 5-10 g/L of peptone, 5-15 g/L of KH$_2$PO$_4$, 2-5 g/L of MgSO$_4$·7H$_2$O, 5-15 mg/L of FeSO$_4$·7H$_2$O, 5-15 mg/L of MnSO$_4$·H$_2$O, 1-3 mg/L of V$_{B1}$, 0.1-1 mg/L of V$_H$, two drops of a defoamer and the balance water, wherein pH was 7.0-7.2;

a fermentation medium was composed of 10-25 g/L of glucose, 1-5 g/L of yeast extract, 1-5 g/L of peptone, 1-5 g/L of KH$_2$PO$_4$, 1-3 g/L of MgSO$_4$·7H$_2$O, 10-30 mg/L of FeSO$_4$·7H$_2$O, 10-30 mg/L of MnSO$_4$·H$_2$O, 1-3 mg/L of V$_{B1}$, 1-3 mg/L of V$_{B2}$, 1-3 mg/L of V$_{B3}$, 1-3 mg/L of V$_{B5}$, 1-3 mg/L of V$_{B12}$, 1-3 mg/L of V$_H$ and the balance water, wherein pH was 7.0-7.2.

Embodiment 3

A fermentation experiment of *E. coli* WHY3-1 in the 5L tank.

Producing the histidine by taking the strain *E. coli* WHY3-1 constructed in the Embodiment 1 as a production strain:

slant activation: a glycerinum preserved strain was taken and streak inoculation was conducted on the slant culture medium of a test tube, and culture was conducted for 12 h at 37° C.; and then a slant preserved strain was inoculated to an eggplant-shaped flask slant culture medium through streak inoculation, and culture was conducted for 14 h at 37 ° C.;

seed culture: an activated fresh eggplant-shaped flask slant was taken, and the strain was washed by 150 mL of sterile water, then was inoculated to the fermentation tank under protection of a flame, the temperature was controlled at 37° C., ammonia water was fed automatically to control the pH at 7.0, the initial ventilating rate was 2 L/min and the initial stirring rotating speed was 200 rpm, in the culture process, the DO value was maintained between 20% and 30%, and seed was cultured till OD$_{600}$ was about 15;

fermentation tank culture: the seed in the fermentation tank was inoculated to the seed solution according to an inoculation amount of 15% (the seed solution was discharged to 450 mL, and was poured into the sterilized fermentation medium under protection of flame), the temperature was controlled at 35° C., ammonia water (or 20% sulfuric acid) was automatically fed to control pH at 7.0, the initial ventilating rate was 2 L/min, the ventilating ratio was 0.667 vvm and the initial stirring rotating speed was 400 rpm, the dissolved oxygen was controlled at 20-30% by adjusting the rotating speed and the air quantity, GPE was dropwise added manually to deform, and in the fermentation process, 80% of glucose solution was fed, so that sufficient sugar supply was ensured and sugar concentration was not higher than 5 g/L;

a slant culture medium was composed of 1 g/L of glucose, 10 g/L of peptone, 10 g/L of beef extract, 5 g/L of yeast powder, 2.5 g/L of NaCl, 25 g/L of agar and the balance water, wherein pH was 7.0-7.2;

a seed culture medium was composed of 10 g/L of glucose, 5 g/L of yeast extract, 5 g/L of peptone, 5 g/L of $KH_2PO_4$, 2 g/L of $MgSO_4 \cdot 7H_2O$, 10 mg/L of $FeSO_4 \cdot 7H_2O$, 10 mg/L of $MnSO_4 \cdot H_2O$, 2 mg/L of $V_{B1}$, 1 mg/L of $V_H$, two drops of a defoamer and the balance water, wherein pH was 7.0-7.2;

a fermentation medium was composed of 10 g/L of glucose, 5 g/L of yeast extract, 4 g/L of tryptone, 3 g/L of $KH_2PO_4$, 1.5 g/L of $MgSO_4 \cdot 7H_2O$, 20 mg/L of $FeSO_4 \cdot 7H_2O$, 20 mg/L of $MnSO_4 \cdot H_2O$, 2 mg/L of $V_{B1}$, 2 mg/L of $V_{B3}$, 2 mg/L of $V_{B5}$, 2 mg/L of $V_{B12}$, 2 mg/L of $V_H$ and the balance water, wherein pH was 7.0-7.2.

Figure 9:
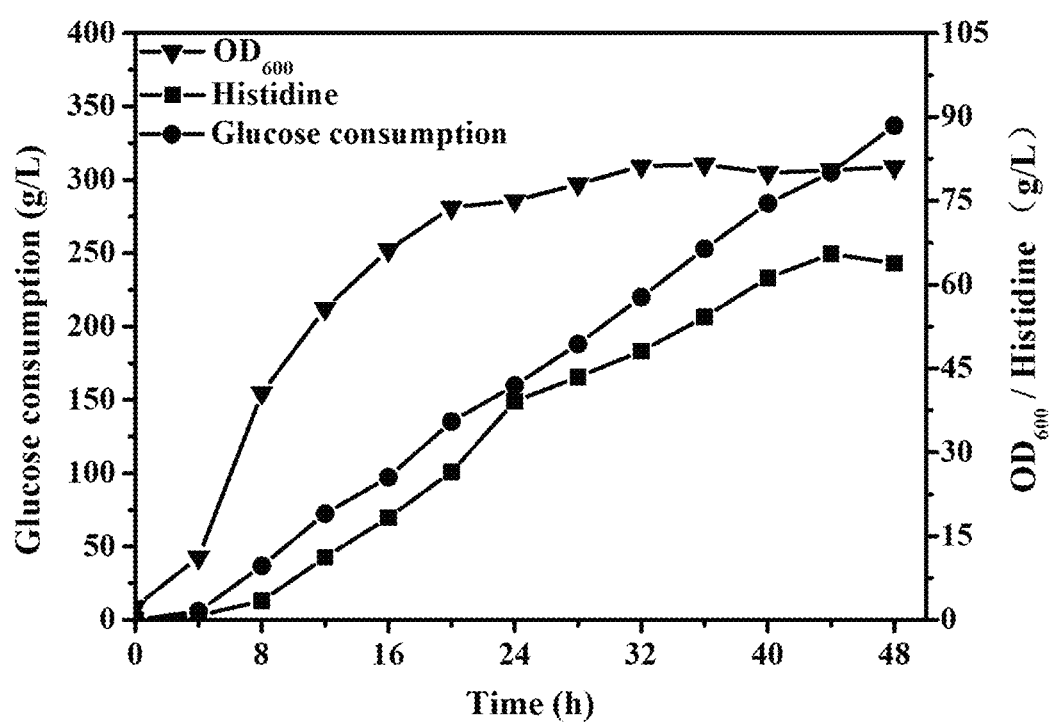
FIG. 9 is a fermentation result of *E. coli* WHY3-1 in a 5 L tank.

A fermentation curve of *E. coli* WHY3-1 on the 5 L fermentation tank is as shown in the FIG. 9.

It can be seen from the fermentation curve that the thalli start to enter a logarithmic phase after being fermented for 4 hours and enter a stable phase in 32 hours after the $OD_{600}$ reaches the maximum value. After fermentation for 8 hours, a quick accumulating stage of histidine is started, and the highest output of histidine after fermentation for 44 hours is 65 g/L. The final conversion ratio is 0.223 g histidine/g glucose. Compared with WHY3 under a same fermentation condition, the biomass of WHY3-1 is reduced, but the output and the production intensity of histidine are improved by 18.2% and the conversion ratio is increased by 11.5%. It can be seen that *E. coli* WHY3-1 as a producing strain for histidine has extremely obvious advantages.

What is claimed is:

1. A genetically engineered *Escherichia coli* for producing L-histidine, wherein the genetically engineered *Escherichia coli* is constructed by taking the genome of *Escherichia coli* as a template and integrating a mutant encoding gene hisG* encoding the *Corynebacterium glutamicum* ATP phosphoribosyl transferase HisG onto the genome allowing for over-expression, wherein the mutant encoding gene hisG* has the nucleotide sequence as shown in SEQ ID NO: 1;

over-expressing by means of increasing the number of histidine operon genes of the *Escherichia coli* on the genome, wherein the histidine operon genes comprise hisD, hisB, hisC, hisH, hisA, hisF and hisI;

integrating an encoding gene lysE from an arginine/lysine transport protein of the *Corynebacterium glutamicum* onto the genome and being over-expressed; and integrating an encoding gene rocG of glutamate dehydrogenase of *Bacillus subtilis* integrated onto the genome and being over-expressed.

2. The genetically engineered *Escherichia coli* for producing L-histidine according to claim 1, wherein the *Escherichia coli* is *Escherichia coli* W3110.

3. The genetically engineered *Escherichia coli* for producing L-histidine according to claim 1, wherein the mutant encoding gene hisG* of the *Corynebacterium glutamicum* ATP phosphoribosyl transferase HisG is integrated to at least two gene loci on the bacterium genome and has a promoter.

4. The genetically engineered *Escherichia coli* for producing L-histidine according to claim 2, wherein the mutant encoding gene hisG* of the *Corynebacterium glutamicum* ATP phosphoribosyl transferase HisG is integrated to at least two gene loci on the bacterium genome and has a promoter.

5. The genetically engineered *Escherichia coli* for producing L-histidine according to claim 1, wherein the mutant encoding gene hisG* of the *Corynebacterium glutamicum* ATP phosphoribosyl transferase HisG is integrated to a tdcD gene locus and a ylbE gene locus on the genome respectively and has a promoter $P_{trc}$;

the histidine operon genes hisD, hisB, hisC, hisH, hisA, hisF and hisI of the *Escherichia coli* are successively integrated to a yghX gene locus on the genome in sequence and have a promoter $P_{trc}$;

the encoding gene lysE of the arginine/lysine transport protein is integrated to a yjiT gene locus on the genome and has a promoter $P_{trc}$; and the encoding gene rocG of the glutamate dehydrogenase is integrated to a yjhE gene locus on the genome of the *Escherichia coli* and has a promoter $P_{trc}$.

6. The genetically engineered *Escherichia coli* for producing L-histidine according to claim 2, wherein the mutant encoding gene hisG* of the *Corynebacterium glutamicum* ATP phosphoribosyl transferase HisG is integrated to a tdcD gene locus and a ylbE gene locus on the genome respectively and has a promoter $P_{trc}$;

the histidine operon genes hisD, hisB, hisC, hisH, hisA, hisF and hisI of the *Escherichia coli* are successively integrated to a yghX gene locus on the genome in sequence and have a promoter $P_{trc}$;

the encoding gene lysE of the arginine/lysine transport protein is integrated to a yjiT gene locus on the genome and has a promoter $P_{trc}$; and the encoding gene rocG of the glutamate dehydrogenase is integrated to a yjhE gene locus on the genome of the *Escherichia coli* and the has a promoter $P_{trc}$.

7. A method for fermentation production of L-histidine, comprising adding the genetically engineered *Escherichia coli* according to claim 1 to a fermentation tank or medium.

8. The method according to claim 7, wherein the *Escherichia coli* is *Escherichia coli* W3110.

9. The method according to claim 7, wherein the mutant encoding gene hisG* of the *Corynebacterium glutamicum* ATP phosphoribosyl transferase HisG is integrated to at least two gene loci on the genome and has a promoter.

10. The method according to claim 8, wherein the mutant encoding gene hisG* of the *Corynebacterium glutamicum* ATP phosphoribosyl transferase HisG is integrated to at least two gene loci on the genome and has a promoter.

11. The method according to claim 7, wherein the mutant encoding gene hisG* of the *Corynebacterium glutamicum* ATP phosphoribosyl transferase HisG is integrated to a tdcD gene locus and a ylbE gene locus on the genome respectively and has a promoter $P_{trc}$;

the histidine operon genes hisD, hisB, hisC, hisH, hisA, hisF and hisI of the *Escherichia coli* are successively integrated to a yghX gene locus on the genome in sequence and have a promoter $P_{trc}$;

the encoding gene lysE of the arginine/lysine transport protein is integrated to a yjiT gene locus on the genome and has a promoter $P_{trc}$; and the encoding gene rocG of the glutamate dehydrogenase is integrated to a yjhE gene locus on the genome of the *Escherichia coli* and has a promoter $P_{trc}$.

12. The method according to claim 8, wherein the mutant encoding gene hisG* of the *Corynebacterium glutamicum* ATP phosphoribosyl transferase HisG is integrated to a tdcD gene locus and a ylbE gene locus on the genome respectively and has a promoter $P_{trc}$;

the histidine operon genes hisD, hisB, hisC, hisH, hisA, hisF and hisI of the *Escherichia coli* are successively integrated to a yghX gene locus on the genome in sequence and have a promoter $P_{trc}$;

the encoding gene lysE of the arginine/lysine transport protein is integrated to a yjiT gene locus on the genome and has a promoter $P_{trc}$; and the encoding gene rocG of the glutamate dehydrogenase is integrated to a yjhE gene locus on the genome of the *Escherichia coli* and has a promoter $P_{trc}$.

* * * * *

```
                        SEQUENCE LISTING

<160> NUMBER OF SEQ ID NOS: 47

<210> SEQ ID NO 1
<211> LENGTH: 627
<212> TYPE: DNA
<213> ORGANISM: Artificial Sequence
<220> FEATURE:
<223> OTHER INFORMATION: The sequence is synthesized

<400> SEQUENCE: 1
atgttgaaaa tcgctgtccc aaacaaaggc tcgctgtccg agcgcgccat ggaaatcctc      60
gccgaagcag gctacgcagg ccgtggagat tccaaatccc tcaacgtttt tgatgaagca     120
aacaacgttg aattcttctt ccttcgccct aaagatatcg ccatctacgt tgctggtggc     180
cagctcgatt tgggtatcac cggccgcgac cttgctcgcg attcccaggc tgatgtccac     240
gaagttcttt ccctcggctt cggttcctcc actttccgtt acgcagcacc agctgatgaa     300
gagtggagca tcgaaaagct cgacggcaag cgcatcgcta cctcttaccc caaccttgtt     360
cgcgatgacc tcgcagcacg tgggctttcc gctgaggtgc tccgcctcga cggtgcagta     420
gaggtattca tcaagcttgg tgtcgcagat gccatcgccg atgttgtatc caccggccgc     480
acgctgcgtc agcaaggtct tgcacctttc ggcgaggttc tgtgcacctc tgaggctgtc     540
attgttggcc gcaaggatga aaaggtcacc ccagagcagc agatcctgct tcgccgcatc     600
cagggaattt tgcacgcgca gaactag                                         627

<210> SEQ ID NO 2
<211> LENGTH: 25
<212> TYPE: DNA
<213> ORGANISM: Artificial Sequence
<220> FEATURE:
<223> OTHER INFORMATION: The sequence is synthesized

<400> SEQUENCE: 2
tattcaaaac agaaaaaccg tcagt                                            25

<210> SEQ ID NO 3
<211> LENGTH: 78
<212> TYPE: DNA
<213> ORGANISM: Artificial Sequence
<220> FEATURE:
<223> OTHER INFORMATION: The sequence is synthesized

<400> SEQUENCE: 3
aattgttatc cgctcacaat tccacacatt atacgagccg gatgattaat tgtcaaggca     60
```
aatcgcgaag aagtacag                                                    78

<210> SEQ ID NO 4
<211> LENGTH: 81
<212> TYPE: DNA
<213> ORGANISM: Artificial Sequence
<220> FEATURE:
<223> OTHER INFORMATION: The sequence is synthesized

<400> SEQUENCE: 4
tccggctcgt ataatgtgtg gaattgtgag cggataacaa tttcacacag gaaacagacc      60
atgttgaaaa tcgctgtccc a                                                81

<210> SEQ ID NO 5
<211> LENGTH: 83
<212> TYPE: DNA
<213> ORGANISM: Artificial Sequence
<220> FEATURE:
<223> OTHER INFORMATION: The sequence is synthesized

<400> SEQUENCE: 5
caccgacaaa caacagataa acgaaaggc ccagtctttc gactgagcct ttcgttttat       60
ttgctagttc tgcgcgtgca aaa                                              83

<210> SEQ ID NO 6
<211> LENGTH: 87
<212> TYPE: DNA
<213> ORGANISM: Artificial Sequence
<220> FEATURE:
<223> OTHER INFORMATION: The sequence is synthesized

<400> SEQUENCE: 6
aaagactggg cctttcgttt tatctgttgt tgtcggtga acgctctcct gagtaggaca       60
aattgaataa tcgctctaac tcctgtg                                          87

<210> SEQ ID NO 7
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 7
cgccctggtt atgggtttt                                                   19

<210> SEQ ID NO 8
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 8
acccaacctt acgcaaccag                                                  20

<210> SEQ ID NO 9
<211> LENGTH: 76
<212> TYPE: DNA
<213> ORGANISM: Artificial Sequence
<220> FEATURE:
<223> OTHER INFORMATION: The sequence is synthesized

<400> SEQUENCE: 9
aattgttatc cgctcacaat tccacacatt atacgagccg gatgattaat tgtcaattgt    60
tcgataaccg cagcat    76

<210> SEQ ID NO 10
<211> LENGTH: 80
<212> TYPE: DNA
<213> ORGANISM: Artificial Sequence
<220> FEATURE:
<223> OTHER INFORMATION: The sequence is synthesized

<400> SEQUENCE: 10
aaagactggg cctttcgttt tatctgttgt ttgtcggtga acgctctcct gagtaggaca    60
aatcgctggc gtgctttgaa    80

<210> SEQ ID NO 11
<211> LENGTH: 19
<212> TYPE: DNA
<213> ORGANISM: Artificial Sequence
<220> FEATURE:
<223> OTHER INFORMATION: The sequence is synthesized

<400> SEQUENCE: 11
ggcgtaactc agcaggcag    19

<210> SEQ ID NO 12
<211> LENGTH: 23
<212> TYPE: DNA
<213> ORGANISM: Artificial Sequence
<220> FEATURE:
<223> OTHER INFORMATION: The sequence is synthesized

<400> SEQUENCE: 12
tttgttctct tcgacctgat gac    23

<210> SEQ ID NO 13
<211> LENGTH: 77
<212> TYPE: DNA
<213> ORGANISM: Artificial Sequence
<220> FEATURE:
<223> OTHER INFORMATION: The sequence is synthesized

<400> SEQUENCE: 13
aattgttatc cgctcacaat tccacacatt atacgagccg gatgattaat tgtcaactgt    60
tctacgttgc gcttttt    77

<210> SEQ ID NO 14
<211> LENGTH: 85
<212> TYPE: DNA
<213> ORGANISM: Artificial Sequence
<220> FEATURE:
<223> OTHER INFORMATION: The sequence is synthesized

<400> SEQUENCE: 14
tccggctcgt ataatgtgtg gaattgtgag cggataacaa tttcacacag gaaacagacc    60
atgagcttta acacaatcat tgact    85

<210> SEQ ID NO 15
<211> LENGTH: 83
<212> TYPE: DNA
<213> ORGANISM: Artificial Sequence
<220> FEATURE:
<223> OTHER INFORMATION: The sequence is synthesized

<400> SEQUENCE: 15

```
gccccaaggg gttatgctag cctacaaatt gagttatgtt catttaaata tgatgttgtt    60
cagtcatgct tgctccttaa ggg                                            83
```

<210> SEQ ID NO 16
<211> LENGTH: 89
<212> TYPE: DNA
<213> ORGANISM: Artificial Sequence
<220> FEATURE:
<223> OTHER INFORMATION: The sequence is synthesized

<400> SEQUENCE: 16

```
ctgaacaaca tcatatttaa atgaacataa ctcaatttgt aggctagcat aaccccttgg    60
ggcgtcatag taatccagca actcttgtg                                      89
```

<210> SEQ ID NO 17
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 17

```
gagcaggtat ttacgtgaac cg                                             22
```

<210> SEQ ID NO 18
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 18

```
atttcgtggc ttctgatttg ct                                             22
```

<210> SEQ ID NO 19
<211> LENGTH: 85
<212> TYPE: DNA
<213> ORGANISM: Artificial Sequence
<220> FEATURE:
<223> OTHER INFORMATION: The sequence is synthesized

<400> SEQUENCE: 19

```
agttgctgga ttactatgac cctagaagaa atcaaccagc gcatcagaaa gtctcctgtg    60
catttacagc actcctttcg acgag                                          85
```

<210> SEQ ID NO 20
<211> LENGTH: 89
<212> TYPE: DNA
<213> ORGANISM: Artificial Sequence
<220> FEATURE:
<223> OTHER INFORMATION: The sequence is synthesized

<400> SEQUENCE: 20

```
atgcacagga gactttctga tgcgctggtt gatttcttct agggtcatag taatccagca    60
actgtcatag taatccagca actcttgtg                                      89
```

<210> SEQ ID NO 21
<211> LENGTH: 22
<212> TYPE: DNA
<213> ORGANISM: Artificial Sequence
<220> FEATURE:
<223> OTHER INFORMATION: The sequence is synthesized

<400> SEQUENCE: 21
gtgaccgtta cgctcacgta gt    22

<210> SEQ ID NO 22
<211> LENGTH: 83
<212> TYPE: DNA
<213> ORGANISM: Artificial Sequence
<220> FEATURE:
<223> OTHER INFORMATION: The sequence is synthesized

<400> SEQUENCE: 22
caccgacaaa caacagataa aacgaaaggc ccagtctttc gactgagcct ttcgttttat    60
ttgtcactga tgccgtttac gca    83

<210> SEQ ID NO 23
<211> LENGTH: 89
<212> TYPE: DNA
<213> ORGANISM: Artificial Sequence
<220> FEATURE:
<223> OTHER INFORMATION: The sequence is synthesized

<400> SEQUENCE: 23
aaagactggg cctttcgttt tatctgttgt tgtcggtga acgctctcct gagtaggaca    60
aatgtcatag taatccagca actcttgtg    89

<210> SEQ ID NO 24
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 24
aatagttgtt gccgcctgag t    21

<210> SEQ ID NO 25
<211> LENGTH: 76
<212> TYPE: DNA
<213> ORGANISM: Artificial Sequence
<220> FEATURE:
<223> OTHER INFORMATION: The sequence is synthesized

<400> SEQUENCE: 25
aattgttatc cgctcacaat tccacacatt atacgagccg gatgattaat tgtcaaaaaa    60
caggcagcaa agtccc    76

<210> SEQ ID NO 26
<211> LENGTH: 85
<212> TYPE: DNA
<213> ORGANISM: Artificial Sequence
<220> FEATURE:
<223> OTHER INFORMATION: The sequence is synthesized

<400> SEQUENCE: 26
tccggctcgt ataatgtgtg gaattgtgag cggataacaa tttcacacag gaaacagacc    60
atggtgatca tggaaatctt catta    85

<210> SEQ ID NO 27
<211> LENGTH: 88
<212> TYPE: DNA
<213> ORGANISM: Artificial Sequence
<220> FEATURE:
<223> OTHER INFORMATION: The sequence is synthesized

```
<400> SEQUENCE: 27
caccgacaaa caacagataa aacgaaaggc ccagtctttc gactgagcct ttcgttttat      60
ttgctaaccc atcaacatca gtttgatg                                        88

<210> SEQ ID NO 28
<211> LENGTH: 86
<212> TYPE: DNA
<213> ORGANISM: Artificial Sequence
<220> FEATURE:
<223> OTHER INFORMATION: The sequence is synthesized

<400> SEQUENCE: 28
aaagactggg cctttcgttt tatctgttgt tgtcggtga acgctctcct gagtaggaca      60
aataagcact acctgtgaag ggatgt                                          86

<210> SEQ ID NO 29
<211> LENGTH: 21
<212> TYPE: DNA
<213> ORGANISM: Artificial Sequence
<220> FEATURE:
<223> OTHER INFORMATION: The sequence is synthesized

<400> SEQUENCE: 29
cagggcttcc acagtcacaa t                                               21

<210> SEQ ID NO 30
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 30
agtcctaggt ataatactag taaaagagat gaatgaattt cgttttagag ctagaa         56

<210> SEQ ID NO 31
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 31
ttctagctct aaaacgaaat tcattcatct cttttactag tattatacct aggact         56

<210> SEQ ID NO 32
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 32
agtcctaggt ataatactag tacactggct ggatgtgcaa cgttttagag ctagaa         56

<210> SEQ ID NO 33
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 33
```
ttctagctct aaaacgttgc acatccagcc agtgtactag tattatacct aggact      56

<210> SEQ ID NO 34
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 34
agtcctaggt ataatactag tggtgcctga cgaccataaa agttttagag ctagaa      56

<210> SEQ ID NO 35
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 35
ttctagctct aaaactttta tggtcgtcag gcaccactag tattatacct aggact      56

<210> SEQ ID NO 36
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 36
agtcctaggt ataatactag tatgaacata actcaatttg tgttttagag ctagaa      56

<210> SEQ ID NO 37
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 37
ttctagctct aaaacacaaa ttgagttatg ttcatactag tattatacct aggact      56

<210> SEQ ID NO 38
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 38
agtcctaggt ataatactag ttgcgctggt tgatttcttc tgttttagag ctagaa      56

<210> SEQ ID NO 39
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 39
ttctagctct aaaacagaag aaatcaacca gcgcaactag tattatacct aggact      56

<210> SEQ ID NO 40
<211> LENGTH: 56
<212> TYPE: DNA
<213> ORGANISM: Artificial Sequence

```
<220> FEATURE:
<223> OTHER INFORMATION: The sequence is synthesized

<400> SEQUENCE: 40
agtcctaggt ataatactag tagggattat gaacggcaat ggttttagag ctagaa        56

<210> SEQ ID NO 41
<211> LENGTH: 56
<212> TYPE: DNA
<213> ORGANISM: Artificial Sequence
<220> FEATURE:
<223> OTHER INFORMATION: The sequence is synthesized

<400> SEQUENCE: 41
ttctagctct aaaaccattg ccgttcataa tccctactag tattataccT aggact        56

<210> SEQ ID NO 42
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 42
gtcaggcact ggcgaaagat                                                20

<210> SEQ ID NO 43
<211> LENGTH: 75
<212> TYPE: DNA
<213> ORGANISM: Artificial Sequence
<220> FEATURE:
<223> OTHER INFORMATION: The sequence is synthesized

<400> SEQUENCE: 43
aattgttatc cgctcacaat tccacacatt atacgagccg gatgattaat tgtcaacgca    60
agccataaac ccaca                                                     75

<210> SEQ ID NO 44
<211> LENGTH: 82
<212> TYPE: DNA
<213> ORGANISM: Artificial Sequence
<220> FEATURE:
<223> OTHER INFORMATION: The sequence is synthesized

<400> SEQUENCE: 44
tccggctcgt ataatgtgtg gaattgtgag cggataacaa tttcacacag gaaacagacc    60
atgtcagcaa agcaagtctc ga                                             82

<210> SEQ ID NO 45
<211> LENGTH: 82
<212> TYPE: DNA
<213> ORGANISM: Artificial Sequence
<220> FEATURE:
<223> OTHER INFORMATION: The sequence is synthesized

<400> SEQUENCE: 45
caccgacaaa caacagataa aacgaaaggc ccagtctttc gactgagcct ttcgttttat    60
ttgttagacc catccgcgga aa                                             82

<210> SEQ ID NO 46
<211> LENGTH: 77
<212> TYPE: DNA
<213> ORGANISM: Artificial Sequence
<220> FEATURE:
```

```
<223> OTHER INFORMATION: The sequence is synthesized

<400> SEQUENCE: 46
ctgggccttt cgttttatct gttgtttgtc ggtgaacgct ctcctgagta ggacaaattt      60
ccgacatcga aatgcgt                                                    77

<210> SEQ ID NO 47
<211> LENGTH: 20
<212> TYPE: DNA
<213> ORGANISM: Artificial Sequence
<220> FEATURE:
<223> OTHER INFORMATION: The sequence is synthesized

<400> SEQUENCE: 47
aggcgttgtt gtggcagatt                                                 20
```